(12) United States Patent
Hasegawa

(10) Patent No.: US 8,094,308 B2
(45) Date of Patent: Jan. 10, 2012

(54) SPECTROMETRIC ANALYZING DEVICE AND SPECTROMETRIC ANALYZING METHOD

(75) Inventor: Takeshi Hasegawa, Tokyo (JP)

(73) Assignee: Tokyo Institute of Technology, Tokyo (JP)

( * ) Notice: Subject to any disclaimer, the term of this patent is extended or adjusted under 35 U.S.C. 154(b) by 257 days.

(21) Appl. No.: 12/310,865

(22) PCT Filed: Dec. 21, 2007

(86) PCT No.: PCT/JP2007/001453
§ 371 (c)(1),
(2), (4) Date: Mar. 9, 2009

(87) PCT Pub. No.: WO2008/099442
PCT Pub. Date: Aug. 21, 2008

(65) Prior Publication Data
US 2009/0316152 A1    Dec. 24, 2009

(30) Foreign Application Priority Data

Feb. 16, 2007  (JP) .................................. 2007-037051

(51) Int. Cl.
*G01J 4/00* (2006.01)
(52) U.S. Cl. ........................................... 356/364
(58) Field of Classification Search .................. None
See application file for complete search history.

(56) References Cited

U.S. PATENT DOCUMENTS
3,926,524 A * 12/1975 Margulies et al. ............ 356/364
(Continued)

FOREIGN PATENT DOCUMENTS
JP    4-363645 A    12/1992
(Continued)

OTHER PUBLICATIONS

Hasegawa et al "Optimum Condition of Fourier Tranform Infrafed Multiple-Angle Incidence Resolution Spectrometry for Surface Analysis", Analytical Chemistry, Dec. 1, 2002, vol. 74, No. 23, pp. 6049-6054.

(Continued)

*Primary Examiner* — Gregory J Toatley
*Assistant Examiner* — Juan D Valentin
(74) *Attorney, Agent, or Firm* — Wells St. John P.S.

(57) ABSTRACT

A spectrometric analyzing device is capable of analyzing a thin film with high accuracy by using light having an arbitrary wavelength, such as not only infrared light but also visible light, ultraviolet light and X-ray, and using whatever refractive index of a supporting member of the thin film. A spectrometric analyzing device comprises a light source (1), a polarizing filter (2), a detection unit (3), a regression operation unit (4) and an absorbance spectrum calculation unit (5). The light source (1) emits light at n different angles of incidence ($\theta_n$) to a measurement portion. The polarizing filter (2) shields an s-polarized component. The detection unit (3) detects transmitted spectra (S). The regression operation unit (4) uses the transmitted spectra (S) and a mixing ratio (R) to obtain an in-plane mode spectrum ($s_{ip}$) and an out-of-plane mode spectrum ($s_{op}$) through a regression analysis. The absorbance spectrum calculation unit (5) calculates an in-plane mode absorbance spectrum ($A_{ip}$) and an out-of-plane mode absorbance spectrum ($A_{op}$) of the thin film, based on the results from a state in which the thin film is on the supporting member and a state in which no thin film is on the supporting member.

8 Claims, 4 Drawing Sheets

U.S. PATENT DOCUMENTS

| | | | |
|---|---|---|---|
| 5,373,359 A | 12/1994 | Woollam et al. | |
| 5,504,582 A | 4/1996 | Johs et al. | |
| 5,521,706 A | 5/1996 | Green et al. | |
| 6,452,680 B1 * | 9/2002 | Paldus et al. | 356/436 |
| 6,937,341 B1 * | 8/2005 | Woollam et al. | 356/436 |
| 7,799,571 B2 * | 9/2010 | Soleta et al. | 436/104 |
| 2006/0262313 A1 * | 11/2006 | Bahatt et al. | 356/445 |

FOREIGN PATENT DOCUMENTS

| | | | |
|---|---|---|---|
| JP | 5-296920 A | 11/1993 | |
| JP | 8-105716 A | 4/1996 | |
| JP | 9-218133 A | 8/1997 | |
| JP | 2003-90762 A | 3/2003 | |
| JP | 2005-003386 A | 6/2005 | |
| JP | 2006-214778 A | 8/2006 | |

OTHER PUBLICATIONS

Hasegawa, "Advanced Multiple-Angle Incidence Resolution Spectrometry for Thin-Layer Analysis on a Low-Refractive-Index Substrate", Analytical chemistry, Jun. 15, 2007, vol. 79, No. 12, pp. 4385-4389.

Hasegawa, "Keiryo Kagaku ga Hiraku Atarashii Kaimen no Hikari Keisoku", Seibutsu Kogaku, Apr. 25, 2006, vol. 84, No. 4, pp. 134-137.

* cited by examiner

SPECTROMETRIC ANALYZING DEVICE AND SPECTROMETRIC ANALYZING METHOD

CROSS REFERENCE TO RELATED APPLICATION

This is a 35 U.S.C. §371 application of and claims priority to International Application No. PCT/JP2007/001453, which was filed on Dec. 21, 2007, and which claims priority to Japanese Patent Application No. 2007-037051, which was filed on Feb. 16, 2007, and the teachings of all the applications are incorporated herein by reference.

TECHNICAL FIELD

The present invention relates to a spectrometric analyzing device and a spectrometric analyzing method, and more particularly to a spectrometric analyzing device and a spectrometric analyzing method for analyzing molecular orientation in a thin film on a supporting member.

BACKGROUND ART

Thin films made of, for example, polyimide, porphyrin, sexiphenyl, sexithienyl, polytetrafluoroethylene, etc. are known as functional organic materials. These thin films are known to improve functions of films or add new functions when molecules are oriented and aligned in a particular direction. Various techniques for controlling molecular orientation have hence been developed. A technique for analyzing molecular orientation in a thin film is important for making such control on molecular orientation. To analyze molecular orientation in a functional organic material and to accurately grasp an in-plane structure of atoms near a surface of a thin film are important in studies of functional materials and biotechnology.

Fourier transform infrared spectrometry, soft X-ray absorption spectrometry, ultraviolet photoelectron spectrometry, etc. are known as such an analytical method of molecular orientation. It is known as a method capable of more accurate analysis that multiple-angle incidence resolution spectrometry (MAIRS) is capable of analyzing a thin film on a supporting member having a high-refractive index with high accuracy in combination with infrared spectrometry (see Patent Document 1 and Non-Patent Document 1). This method is to obtain, as two independent spectra, transition moments which are respectively parallel and perpendicular to the thin film when spectra of the thin film are measured by absorption spectrometry. In the case of infrared spectrometry, the aforementioned transition moments parallel and perpendicular to the thin film may be said to be oscillations of a functional group parallel and perpendicular to the thin film. In the multiple-angle incidence resolution spectrometry, unpolarized light is incident on the thin film at several angles of incidence. By analyzing transmitted spectra of the unpolarized light, the unpolarized light is converted into an ordinary ray (light having an electric field oscillation perpendicular to the traveling direction of the light) and a virtual ray (light having an electric field oscillation in the traveling direction of the light). Only by comparing the two spectra, it can easily be analyzed how much each functional group is oriented.

Patent Document 1: Japanese Patent Application Kokai Publication No. 2003-90762.

Non-Patent Document 1: Takeshi Hasegawa, "A Novel Optical Technique for Analysis of Surface and Interface Developed by Using Chemometrics", Journal of the Society for Biotechnology, April 2006, Vol. 84, No. 4, Pages 134 to 137.

DISCLOSURE OF THE INVENTION

Problems to be Solved by the Invention

Although such conventional multiple-angle incidence resolution spectrometry has produced satisfactory results of the thin film analysis on a supporting member having a high refractive index, the theory of MAIRS has been logically and experimentally found to fail when the thin film analysis is carried out on a supporting member having a low refractive index. One of the factors that cause such a failure is a problem that light which is multiply reflected inside the supporting member is lead to the transmitted spectrum detection unit when the refractive index of the supporting member of the thin film is low. Specifically, the supporting member therefore needs to have a refractive index, n, of 2.5 or higher, in the case of the conventional multiple-angle incidence resolution spectrometry using infrared light. Consequently, a germanium substrate (n=4.0) or a silicon substrate (n=3.5) which has a high refractive index in the infrared region needs to be used. On the other hand, although a calcium fluoride substrate (n=1.40) and a glass substrate (n=1.35) each can form a practically useful supporting member at a lower cost, these substrates have low refractive indexes and therefore cannot be used in the MAIRS analysis.

Further, to realize the multiple-angle incidence resolution spectrometry with the use of not only infrared light but also visible light or ultraviolet light, the aforementioned problem concerning the refractive index becomes more pronounced. That is, in the ultraviolet or visible region, most supporting members have a smaller refractive index than 2. Therefore, thin film analysis by MAIRS cannot be carried out in theory.

Developments hence have been made in devices and methods which are capable of analyzing thin films with high accuracy, independent of the refractive index of the supporting member and independent of wavelength of the light source.

In view of the circumstances as described above, the present invention has as its object to provide a spectrometric analyzing device and a spectrometric analyzing method which are capable of analyzing a thin film with high accuracy by using light having an arbitrary wavelength, such as not only infrared light but also visible light, ultraviolet light and X-ray, and using whatever refractive index of a supporting member of the thin film.

Means for Solving the Problems

To achieve the object of the present invention as described above, a spectrometric analysis device according to an aspect of the invention for analyzing a thin film on a supporting member that is optically transparent to incident light comprises: a light source capable of emitting light to a measurement portion to be measured, at n different angles of incidence, $\theta_n$, (where n=3, 4, . . . ); a polarizing filter provided between the light source and the measurement portion and shielding an s-polarized component of the transmitted light; a detection unit receiving transmitted light transmitted through the measurement portion, thereby detecting transmitted spectra, S; a regression operation unit obtaining an in-plane mode spectrum, $s_{ip}$, and an out-of-plane mode spectrum, $s_{op}$, through a regression analysis, by using the transmitted spectra, S, detected by the detection unit for the transmitted light at each of the n different angles of incidence from the light source, and by using a mixing ratio, R, of the in-plane mode spectrum, $s_{ip}$, and the out-of-plane mode spectrum, $s_{op}$, for each of the angles of incidence; and an absorbance spectrum calculation unit calculating an in-plane mode absorbance spectrum, $A_{ip}$, and an out-of-plane mode absorbance spectrum, $A_{op}$, of the thin film, based on the in-plane mode spectrum, $s_{ip}$, and the out-of-plane mode spectrum, $s_{op}$, which are obtained by the regression operation unit in each of a state in which the thin film is on the supporting member and a state in which no thin film is on the supporting member.

Desirably, the regression operation unit may obtain the in-plane mode spectrum, $s_{ip}$, and the out-of-plane mode spectrum, $s_{op}$, through a regression analysis using a regression formula below:

$$\begin{pmatrix} s_{ip} \\ s_{op} \end{pmatrix} = (R^T R)^{-1} R^T S$$

where superscript, T, denotes a transposed matrix and superscript, −1, denotes an inverse matrix.

Also, the mixing ratio, R, may be expressed by a matrix below:

$$R = C \begin{pmatrix} \cos^2\theta_1 + \sin^2\theta_1 \tan^2\theta_1 & \tan^2\theta_1 \\ \cos^2\theta_2 + \sin^2\theta_2 \tan^2\theta_2 & \tan^2\theta_2 \\ \vdots & \vdots \\ \cos^2\theta_j + \sin^2\theta_j \tan^2\theta_j & \tan^2\theta_j \\ \vdots & \vdots \\ \cos^2\theta_n + \sin^2\theta_n \tan^2\theta_n & \tan^2\theta_n \end{pmatrix}$$

where C denotes a constant and $\theta_j$ denotes a j-th angle of incidence among the n different angles of incidence of the light from the light source.

Also, the absorbance spectrum calculation unit may calculate the in-plane mode absorbance spectrum, $A_{ip}$, and the out-of-plane mode absorbance spectrum, $A_{op}$, of the thin film, in a manner that the in-plane mode spectrum, $s_{sip}$, and the out-of-plane mode spectrum, $s_{sop}$, which are obtained with the thin film on the supporting member are respectively divided by the in-plane mode spectrum, $s_{bip}$, and the out-of-plane mode spectrum, $s_{bop}$, which are obtained without the thin film on the supporting member, thereby obtaining logarithms.

Still also, the light source may be capable of emitting the light at the n different angles of incidence, $\theta_n$, within a range from greater than 0° to smaller than an angle at which a sum of a reflectance of the s-polarized component and a reflectance of a p-polarized component of the supporting member begins to exhibit great variation in relation to the angles of incidence.

Also desirably, the light source may be capable of emitting light having an arbitrary wavelength which is optically transparent to the supporting member.

A spectrometric analyzing method according to another aspect of the invention for analyzing a thin film on a supporting member that is optically transparent to incident light, comprises: a step 6f emitting light from a light source to a measurement portion to be measured, at n different angles of incidence, $\theta_n$, (where n=3, 4, . . . ); a step of shielding an s-polarized component of the transmitted light, by using a polarizing filter provided between the light source and the measurement portion; a detection step of receiving transmitted light transmitted through the measurement portion, thereby detecting transmitted spectra, S; a regression operation step of performing a regression analysis, to obtain an in-plane mode spectrum, $s_{ip}$, and an out-of-plane mode spectrum, $s_{op}$, by using the transmitted spectra, S, detected by the detection step for the transmitted light at each of the n different angles of incidence from the light source, and by using a mixing ratio, R, of the in-plane mode spectrum, $s_{ip}$, and the out-of-plane mode spectrum, $s_{op}$, for each of the angles of incidence; and an absorbance spectrum calculation step of calculating an in-plane mode absorbance spectrum, $A_{ip}$, and an out-of-plane mode absorbance spectrum, $A_{op}$, of the thin film, based on the in-plane mode spectrum, $s_{ip}$, and the out-of-plane mode spectrum, $s_{op}$, which are obtained in each of a state in which the thin film is on the supporting member and a state in which no thin film is on the supporting member through the regression operation step.

A program according to still another aspect of the invention may cause a computer to function as the regression operation unit described above.

A program according to still another aspect of the invention may cause a computer to function as the absorbance spectrum calculation unit described above.

Advantages of the Invention

The spectrometric analyzing device and spectrometric analyzing method according to the present invention are advantageous in that whatever refractive index of a supporting member, analysis on molecular orientation in a thin film, to which multiple-angle incidence resolution spectrometry is applied, is available even with the use of light having an arbitrary wavelength, such as, not only light in the infrared region but also light in the visible, ultraviolet, and X-ray regions.

BEST MODE FOR CARRYING OUT THE INVENTION

Now, an embodiment according to the invention is explained with reference to the drawings. FIG. 1 shows a schematic structure, for explaining the overall structure of a spectrometric analyzing device according to the invention. As shown in FIG. 1, the spectrometric analyzing device according to the invention is mainly constituted by a light source 1, a polarizing filter 2, a detection unit 3, a regression operation unit 4, and an absorbance spectrum calculation unit 5. Further, a thin film 6 is provided between the polarizing filter 2 and the detection unit 3, and on a supporting member 7.

The light source 1 is capable of emitting light having a predetermined wavelength to a measurement portion of the thin film 6. The light source 1 can be of any type that emits light having any wavelength, such as infrared, ultraviolet, and X-rays. Since a conventional spectrometric analyzing device needs to employ a supporting member having a high refractive index, light emitted from the light source thereof is limited to infrared ray. However, the light source of the spectrometric analyzing device according to the invention can emit light having an arbitrary wavelength as long as the light is optically transparent to the supporting member. Availability of light of any wavelength enables measurement with the use of a supporting member having any refractive index. That is, in the spectrometric analyzing device according to the invention, thin film analyses are available not only with a supporting member having a higher refractive index than 2.5, but also with a supporting member having a lower refractive index than 2.5. Therefore, light having an arbitrary wavelength with which the light is optically transparent to the supporting member can be used.

The light source 1 has a structure in which light can be emitted to the measurement portion of the thin film 6, with an angle of incidence, θ, of the light from the surface normal changed to other angles. The light source 1 may be pivoted in relation to the thin film 6 to change the angle of incidence, or the supporting member 7 may be pivoted to change the angle of incidence. That is, in whatever manner the angle of incidence of the light from the light source 1 can be changed. The light source 1 can have any other structure as long as the light source 1 is configured to be capable of emitting light to the measured portion at different angles of incidence. Further, the light source 1 needs to be capable of emitting light at least three angles of incidence. As will be described later, the spectrometric analyzing device according to the invention performs a regression analysis by using measured transmitted spectra. Very inaccurate analysis can be performed unless at least three different transmitted spectra are available. Accordingly, the light source 1 is configured to be capable of emitting light to a measurement portion at n different angles of incidence, $\theta_n$, (where n=3, 4, . . . ).

Further, the polarizing filter 2 is provided between the light source 1 and the measurement portion of the thin film 6, and shields an s-polarized component of the light emitted from the light source 1. Referring to FIG. 2, a description will now be made of changes to the s-polarized component and the p-polarized component when the light comes into the thin film 6. FIG. 2 shows characteristics of changes in reflectances of the s-polarized and p-polarized components, in relation to changes of the angle of incidence to the supporting member. The examples in the figure show characteristics in the cases employing a germanium (Ge) and glass substrates used as supporting members. The s-polarized component (s-pol) indicates a polarized component perpendicular to the substrate surface. The p-polarized component (p-pol) indicates a polarized component parallel to the substrate surface. As can be seen from the figure, the reflectance of the p-polarized component becomes remarkably weak at around 40° in comparison with the reflectance of the s-polarized component, in the case of a glass substrate as the supporting member having a low refractive index. Therefore, since the s-polarized component is so large in an unbalanced manner on a supporting member having a low refractive index, the measurement based on the conventional multiple-angle incidence resolution spectrometry becomes unstable. Hence, the spectrometric analyzing device according to the invention is configured so that the polarizing filter 2 is used to shield the s-polarized component and that the multiple-angle incidence resolution spectrometry is carried out with use of only the p-polarized component. Specifically, a wire grid polarizer or a Glan Taylor polarizer may be used for the polarizing filter 2. In this manner, only the p-polarized component can be emitted to the thin film 6. The polarizing filter 2 is not needed to completely shield the s-polarized component but needs only to be capable of restricting influence from the s-polarized component. Every type of commercially available polarizing filter can be used for the polarizing filter 2.

FIG. 3 shows characteristics of changes in a sum of the reflectances of the s- and p-polarized components on the supporting members shown in FIG. 2. As can be seen from the figure, the sum of the reflectances increases from around 30° in the case of the glass substrate. That is, the glass substrate causes the s- and p-polarized components to be unbalanced from around 30 to 35°. Accordingly, in the case of the glass substrate, the angle of incidence, $\theta_n$, may be changed within a range of $0°<\theta_n\leqq 35°$, or more preferably $0°<\theta_n\leqq 30°$. Thus, n different angles of incidence, $\theta_n$, of the light from the light source may be set within a range in which $\theta_n$ is greater than 0° and smaller than an angle at which the sum of the reflectances of the s- and p-polarized components on a supporting member begins to exhibit great variation with an increase of the angles of incidence.

In spectrometric analysis, the absolute intensity of one single-beam spectrum needs to be accurately measured for each of angles of incidence, and therefore, the angles of incidence are desirably changed by steps of 5° or larger. Further, the angles of incidence preferably satisfy three conditions as follows. (1) The maximum angle of the range of angles of incidence is desirably as small as possible in order to avoid an influence of multiple reflections. (2) On the other hand, the maximum angle is desirably as large as possible in order to securely obtain molecular information along an oscillation direction parallel to a traveling direction of light. (3) Further, each of the steps by which the angles of incidence are changed is desirably as large as possible in view of measurement stability. In order to satisfy these conditions, the angles of incidence, $\theta_n$, may be optimized by using a known standard sample in accordance with the refractive index and thickness of the supporting member.

Next, the supporting member 7 is optically transparent to incident light and is capable of supporting the thin film 6. The term "optically transparent" means that light is not absorbed, i.e., an absorption coefficient is close to zero. The absorption coefficient is not always needed to be completely zero, but may be negligibly small relative to the absorption of light in a thin film. Therefore, even a supporting member, which has a high reflectance or a low transmittance, can be used as long as the supporting member is transparent. Even under a condition that the reflectance is so high as to reduce the intensity of light which reaches the detection unit, the spectrometric analyzing device according to the invention is capable of measurement using visible, ultraviolet, and further X-rays, so that the intensity of light from the light source accordingly increases. Therefore, the analysis can be performed with no problem. The supporting member includes, for example, germanium or silicon having a high refractive index, or calcium fluoride or glass having a low refractive index as well. Further, the supporting member may be of a liquid such as water as long as the liquid is transparent. That is, a monomolecular film formed as a thin film on a surface of water can be analyzed as a sample.

The thin film 6 is a sample to be spectrometrically analyzed and is on the supporting member 7. Specific examples of the thin film 6 are, for instance, functional organic materials such as polyimide, porphyrin, sexiphenyl, sexithienyl, and polytetrafluoroethylene. The thin film 6 is not always needed to have an image of a "film". According to the spectrometric analyzing device of the present invention, molecular orientation can be detected even from a layer having a thickness equivalent to one chemical bond. The example in FIG. 1 shows a state of incidence of light to the back side in the case where the thin film 6 is provided on the back surface of the supporting member 7, viewed from the light source 1. The present invention is not limited to this case, but is applicable to a thin film provided on the incident surface of the supporting member, and also thin films provided on the two surfaces of the supporting member.

The detection unit 3 detects transmitted spectra, S, by receiving transmitted light through the thin film 6 and the supporting member 7 on which light originally emitted from the light source 1 is irradiated after passing through the polarizing filter 2. The detection unit 3 may be any detector as long as the detector is capable of detecting the transmitted spectra.

The regression operation unit 4 obtains an in-plane mode spectrum, $s_{ip}$, and an out-of-plane mode spectrum, $s_{op}$, through a regression analysis by using a transmitted spectra, S, and a mixing ratio, R, of the in-plane mode spectrum, $s_{ip}$, and the out-of-plane mode spectrum, $s_{op}$. The transmitted spectrum is detected by the detection unit 3 for the transmitted light at each of respectively different angles of incidence, $\theta_n$, from the light source. Referring to FIG. 4, meanings of the in-plane mode spectrum, $s_{ip}$, and the out-of-plane mode spectrum, $s_{op}$, will now be described. The in-plane mode spectrum, $s_{ip}$, is a spectrum obtained when normal light is subjected to normal-incidence transmission measurement, as shown in FIG. 4A. That is, an electric field vector of the light always oscillates perpendicularly to the travelling direction of the light. On the other hand, the out-of-plane mode spectrum, $s_{op}$, is a spectrum obtained when the virtual light is subjected to normal-incidence transmission measurement, as shown in FIG. 4B. That is, an electric field vector of the light always oscillates parallel to the travelling direction of the light. The out-of-plane mode spectrum, $s_{op}$, is a spectrum measured with the virtual light which cannot be directly measured. However, the in-plane mode spectrum, $s_{ip}$, and the out-of-plane spectrum, $s_{op}$, can be obtained by using the transmitted spectra, S, and the mixing ratio, R, of the in-plane mode spectrum, $s_{ip}$, and the out-of-plane mode spectrum, $s_{op}$, by utilizing a measurement theory based on chemometrics as described below.

A transmitted spectrum, $s_{obs}$, measured at the detection unit for a given angle of incidence can be expressed by the following formula by using the in-plane mode spectrum, $s_{ip}$, and the out-of-plane mode spectrum, $s_{op}$, at the time of measurement, and respective mixing ratios, $r_{ip}$ and $r_{op}$, of the spectra.

$$s_{obs} = s_{ip} r_{ip} + s_{op} r_{op} + U \quad \text{[Formula 1]}$$

where U is a non-linear component which cannot be expressed only by the in-plane mode spectrum, $s_{ip}$, and the out-of-plane mode spectrum, $s_{op}$.

From the above formula, the transmitted spectra, S, can further be expressed by the following formula, as a matrix which collects spectra measured at several different angles of incidence.

$$S \cong \begin{pmatrix} s_{obs1} \\ s_{obs2} \\ \vdots \\ s_{obsn} \end{pmatrix} = \begin{pmatrix} r_{ip1} & r_{op1} \\ r_{ip2} & r_{op2} \\ \vdots & \vdots \\ r_{ipn} & r_{opn} \end{pmatrix} \begin{pmatrix} s_{ip} \\ s_{op} \end{pmatrix} + U \cong R \begin{pmatrix} s_{ip} \\ s_{op} \end{pmatrix} + U \quad \text{[Formula 2]}$$

where R is a matrix which stores mixing ratios, $r_{ip}$ and $r_{op}$, of the in-plane mode spectrum, $s_{ip}$, and the out-of-plane mode spectrum, $s_{op}$, for every angle of incidence.

The above formula is further transformed by a regression analysis into the following regression formula without using the non-linear component, U.

$$\begin{pmatrix} s_{ip} \\ s_{op} \end{pmatrix} = (R^T R)^{-1} R^T S \quad \text{[Formula 3]}$$

where the superscript, T, denotes a transposed matrix and the superscript, −1, denotes an inverse matrix.

From this formula, only a linear component can be extracted by disregarding the non-linear component, U. Accordingly, the in-plane mode spectrum, $s_{ip}$, and the out-of-plane mode spectrum, $s_{op}$, can be obtained if the measured transmitted spectra, S, and the mixing ratio, R, are available.

A further description will now be made below for the mixing ratio, R, i.e., the mixing ratios, $r_{ip}$ and $r_{op}$, for the in-plane mode spectrum, $s_{ip}$, and the out-of-plane mode spectrum, $s_{op}$, at each of angles of incidence, each of which is collected in one matrix. FIG. 5 shows and explains electric field vector components of the incident light that is obliquely irradiated on the surface of the thin film 6. In the invention, the light irradiated on the thin film surface is filtered to have only a p-polarized component by a polarizing filter. Therefore, the s-polarized component of light (electric field, $E_s$) polarized in a direction of 0° is shielded by the polarizing filter so as to have relative intensity of 0. The s-polarized component therefore contributes to neither the in-plane mode spectrum, $s_{ip}$, nor the out-of-plane mode spectrum, $s_{op}$. On the other hand, light (electric field, $E_p$) polarized in a direction of 90° can be decomposed into the components of $\cos \theta$ and $\sin \theta$, depending on the angle of incidence, $\theta$. The $\cos \theta$ component of the light oscillates in a direction parallel to the thin film surface, and the $\sin \theta$ component oscillates in a direction perpendicular to the thin film surface. The $\cos \theta$ component that oscillates in a direction parallel to the thin film surface contributes only to the in-plane mode spectrum, $s_{ip}$, because this component oscillates in a direction parallel to the thin film surface. The $\sin \theta$ component that oscillates in a direction perpendicular to the thin film surface goes across the surface obliquely if oscillation of this component goes in the traveling direction of the light. The electric field, $E_p$, can be decomposed into a virtual component, $\sin \theta \tan \theta$, which oscillates in parallel to the thin film surface and another virtual component, $\tan \theta$, which oscillates perpendicularly to the thin film surface. Accordingly, the virtual component, $\sin \theta \tan \theta$, which oscillates in parallel to the thin film surface contributes to the in-plane mode spectrum, $s_{ip}$, and the virtual component, $\tan \theta$, which oscillates perpendicularly to the thin film surface contributes to the out-of-plane mode spectrum, $s_{op}$.

To summarize operations described above, the in-plane mode spectrum, $s_{ip}$, and the out-of-plane mode spectrum, $s_{op}$, can be summarized as shown in the table below.

TABLE 1

|  | $E_s$ | $E_p$ | |
| --- | --- | --- | --- |
| $s_{ip}$ | 0 | $\sin \theta \tan \theta$ | $\cos \theta$ |
| $s_{op}$ | 0 | $\tan \theta$ | 0 |

Therefore, the mixing ratio, $r_{op}$, of the out-of-plane mode spectrum, $s_{op}$, relative to the mixing ratio, $r_{ip}$, for the in-plane mode spectrum, $s_{ip}$, can be expressed by the following formula, taking into consideration that intensity of each electric field vector is detected as a square thereof.

$$r_{ip} : r_{op} = \sin^2 \theta \tan^2 \theta + \cos^2 \theta : \tan^2 \theta \quad \text{[Formula 4]}$$

From this formula, the matrix, R, which collects the mixing ratios, $r_{ip}$ and $r_{op}$, of the in-plane mode spectrum, $s_{ip}$, and the out-of-plane mode spectrum, $s_{op}$, of the light irradiated at each of angles of incidence, $\theta_n$, can be expressed by the following formula.

$$R = C \begin{pmatrix} \cos^2\theta_1 + \sin^2\theta_1\tan^2\theta_1 & \tan^2\theta_1 \\ \cos^2\theta_2 + \sin^2\theta_2\tan^2\theta_2 & \tan^2\theta_2 \\ \vdots & \vdots \\ \cos^2\theta_j + \sin^2\theta_j\tan^2\theta_j & \tan^2\theta_j \\ \vdots & \vdots \\ \cos^2\theta_n + \sin^2\theta_n\tan^2\theta_n & \tan^2\theta_n \end{pmatrix} \qquad \text{[Formula 5]}$$

where C is a constant, and $\theta_j$ is the j-th angle of incidence (where j=1, 2, ..., n) of n angles of incidence of light from the light source.

Therefore, the regression operation unit 4 of the spectrometric analyzing device according to the invention is capable of obtaining the in-plane mode spectrum, $s_{ip}$, and the out-of-plane mode spectrum, $s_{op}$, through the regression analysis of the above Formula 3, by using the transmitted spectra, S, detected by the detection unit 3 for the transmitted light at each of n different angles of incidence from the light source 1, and the mixing ratio, R, of the in-plane mode spectrum, $s_{ip}$, and the out-of-plane mode spectrum, $s_{op}$, for each of the angles of incidence.

In the case of performing a thin film analysis, light that has penetrated the surface of a thin film is irradiated into the thin film and the supporting member, and causes unexpected complicated phenomena such as absorptions and multiple reflections. To eliminate the influence of such phenomena, the absorbance spectrum calculation unit 5 in the spectrometric analyzing device according to the invention calculates an in-plane mode absorbance spectrum, $A_{ip}$, and an out-of-plane mode absorbance spectrum, $A_{op}$, of the thin film, which can be finally used for analysis of the thin film, by using the in-plane mode spectrum, $s_{ip}$, and the out-of-plane mode spectrum, $s_{op}$, which are calculated for each of a state that the thin film is on a supporting member, and a state that no thin film is on the supporting member. More specifically, an in-plane mode spectrum, $s_{sip}$, and an out-of-plane mode spectrum, $s_{sop}$, in a state where the thin film is on the supporting member are respectively divided by an in-plane mode spectrum, $s_{bip}$, and an out-of-plane mode spectrum, $s_{bop}$, in a state where no thin film is on the supporting member, to obtain logarithms. In this manner, the in-plane mode absorbance spectrum, $A_{ip}$, and the out-of-plane absorbance spectrum, $A_{op}$, of the thin film to be finally used may be obtained. That is, final absorbance spectra, $A_{ip}$ and $A_{op}$, can be obtained by the following formula.

$$A_{ip} = -\log_{10}\left(\frac{s_{sip}}{s_{bip}}\right) \qquad \text{[Formula 6]}$$

$$A_{op} = -\log_{10}\left(\frac{s_{sop}}{s_{bop}}\right)$$

In practice, each division of vectors is carried out as a scalar division at each component.

Firstly, the transmitted spectra, S, may be detected from only the supporting member, and the in-plane mode spectrum, $s_{bip}$, and the out-of-plane mode spectrum, $s_{bop}$, may further be calculated. Thereafter, the transmitted spectra, S, may be detected with a thin film deposited on the supporting member, and the in-plane mode spectrum, $s_{sip}$, and the out-of-plane mode spectrum, $s_{sop}$, may further be calculated. When the in-plane mode spectrum, $s_{bip}$, and out-of-plane mode spectrum, $s_{bop}$, for the supporting member without a thin film are known in advance, the transmitted spectra, S, for the supporting member without a thin film does not need always to be detected.

The above regression operation unit 4 and the absorbance spectrum calculation unit 5 may be programs which cause an electronic calculator such as a computer to function as the regression operation unit 4 and absorbance spectrum calculation unit 5.

FIG. 6 shows a result of measuring a predetermined sample by using the spectrometric analyzing device configured as described above according to the invention. The measured sample used is a calcium fluoride substrate having a low refractive index as the supporting member 7. A monolayer built-up film consisted of five layers made of cadmium stearate was used as the thin film 6 supported on the calcium fluoride substrate. A measurement condition was that a light source emitting infrared light was used as the light source 1, and the measurement portion of the thin film was irradiated by the infrared light, changing an angle of incidence of the light in steps of 5° within the range of 5 to 35°. Under this condition, transmitted spectra were measured while changing the angle of incidence in steps of 5° within the range of 5 to 35° in the state that the thin film 6 was on the supporting member 7 and in the state that no thin film was on the supporting member 7. Total seven in-plane mode spectra, $s_{ip}$, and total seven out-of-plane mode spectra, $s_{op}$, were obtained by the regression operation unit 4. Hence, the in-plane mode absorbance spectrum, $A_{ip}$, and the out-of-plane mode absorbance spectrum, $A_{op}$, of the thin film were calculated by the absorbance spectrum calculation unit 5. FIG. 6 shows MAIRS spectra as an analytical result obtained in this manner. For comparison, FIG. 7 shows a result of analyzing the same sample as described above by the conventional multiple-angle incidence resolution spectrometry.

As can be seen from the result generated from the spectrometric analyzing device according to the invention as shown in FIG. 6, the in-plane mode absorbance spectrum, $A_{ip}$, of the thin film seems no problem and is stable. The out-of-plane mode absorbance spectrum, $A_{op}$, of the thin film seems no problem and is stable, as well. In the figure, the intensity of $A_{ip}$ is doubled for quantitativity. The corrected result excellently agrees with the result of the MAIRS spectra based on the conventional multiple-angle incidence resolution spectrometry, which were measured by using a germanium or silicon substrate having a high refractive index as the supporting member.

FIG. 7 will now be referred to as a result of analyzing the same sample by the conventional multiple-angle incidence resolution spectrometry. The in-plane mode absorbance spectrum (IP) of the thin film seems no problem and is stable. However, the out-of-plane mode absorbance spectrum (OP) of the thin film is deformed greatly due to the influence by using the supporting member having a low refractive index. That is, as shown in the figure, a band which should originally appear at 1,544 cm$^{-1}$ appears very strongly and shifted to 1,547 cm$^{-1}$. In addition, the spectrum is also degraded greatly in shape.

Thus, the conventional multiple-angle incidence resolution spectrometry has been found to be incapable of analyzing a thin film on a supporting member having a low refractive index of n=2.5 or lower, with the use of infrared light. However, the spectrometric analyzing device according to the present invention has been found to be capable of excellently analyzing a thin film even with the use of a supporting member having a low refractive index.

Originally, the conventional multiple-angle incidence resolution spectrometry cannot be applied to measurements with the use of light having a wavelength out of the infrared region. However, the spectrometric analyzing device according to the invention is capable of analyzing a thin film even with the use of light having any wavelength. Specifically, owing to light having an arbitrary wavelength which is optically transparent to the supporting member, the spectrometric analyzing device according to the invention is capable of excellently analyzing a thin film whatever refractive index of the supporting member supporting the thin film. If a light source which emits light in a visible or ultraviolet region or in an X-ray region can be used, a sample can be measured with a very bright light source. The analyzing device can be used for much wider applications.

The spectrometric analyzing device and the spectrometric analyzing method according to the present invention are not limited to the aforementioned examples shown in figures, but may be variously modified without deviating from the scope of the invention.

EXPLANATION OF REFERENCE SYMBOLS

Figure 1:
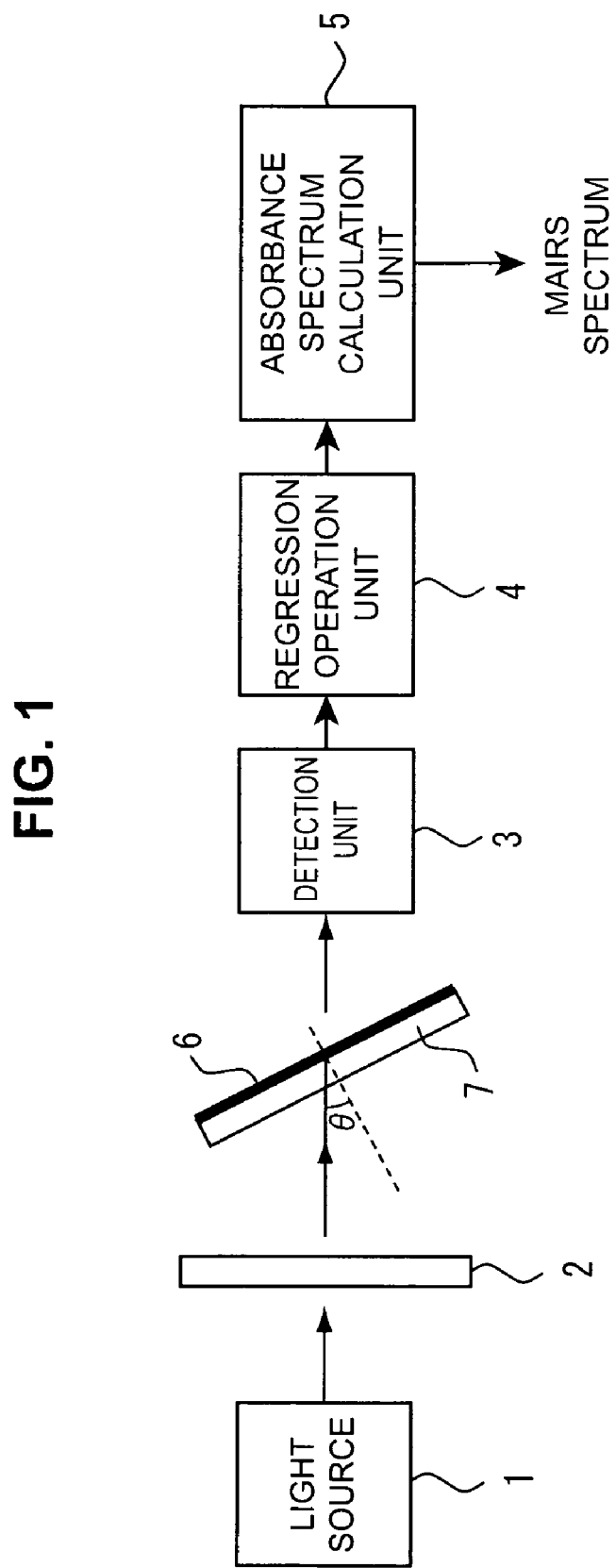
FIG. 1 shows a schematic structure for explaining the whole structure of a spectrometric analyzing device according to the present invention.
Figure 2:
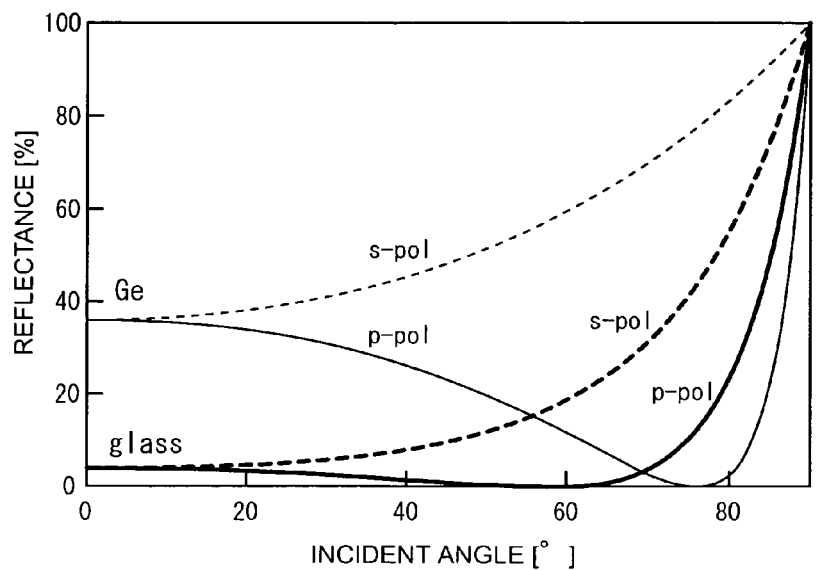
FIG. 2 is a graph showing characteristics in changes of reflectances of s- and p-polarized components in relation to changes of an angle of incidence to a supporting member having a low refractive index.
Figure 3:
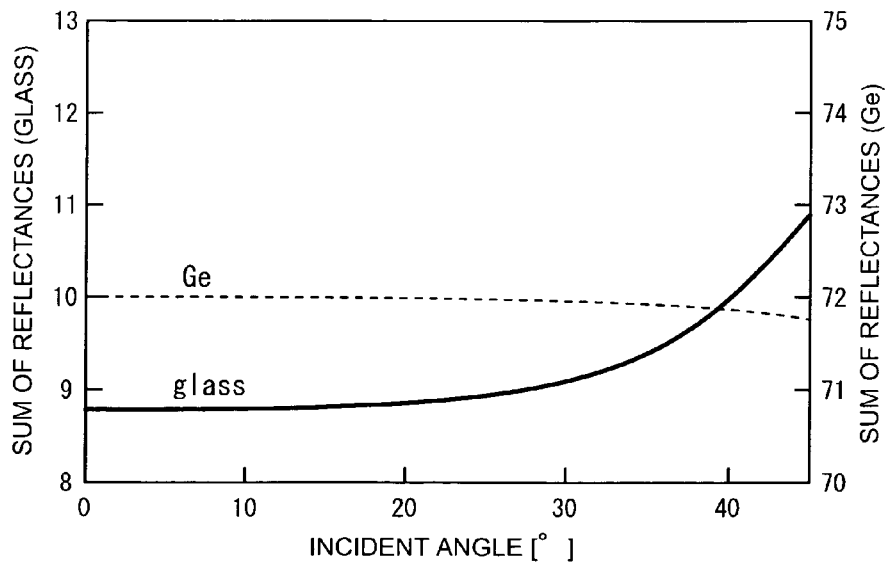
FIG. 3 is a graph showing characteristics in changes of a sum of reflectances of the s- and p-polarized components of the supporting member.
Figure 4A:
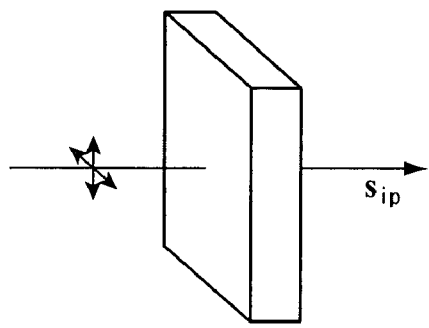
FIG. 4 is a schematic view for explaining meanings of an in-plane mode spectrum, $s_{ip}$, and an out-of-plane mode spectrum, $s_{op}$.
Figure 4B:
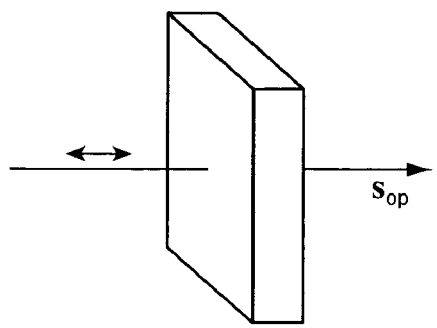
Figure 5:
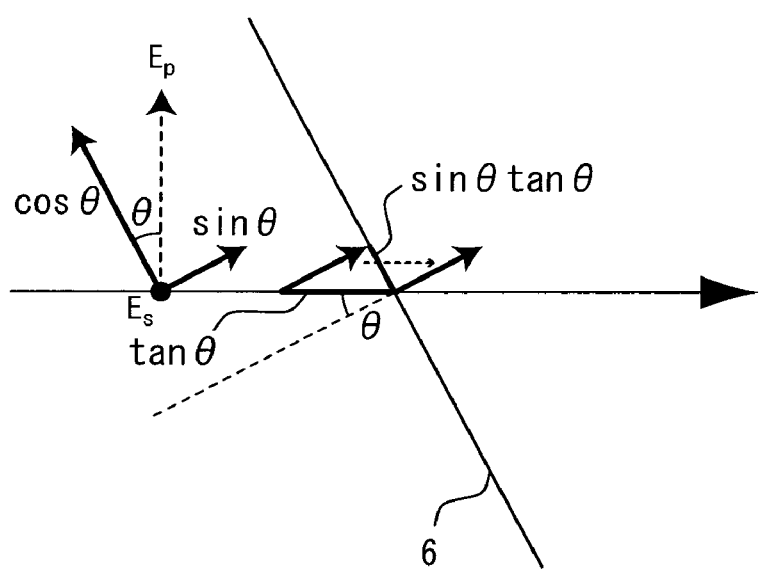
FIG. 5 is a view for explaining electric field vectors of incident light that is obliquely irradiated on the surface of the thin film.
Figure 6:
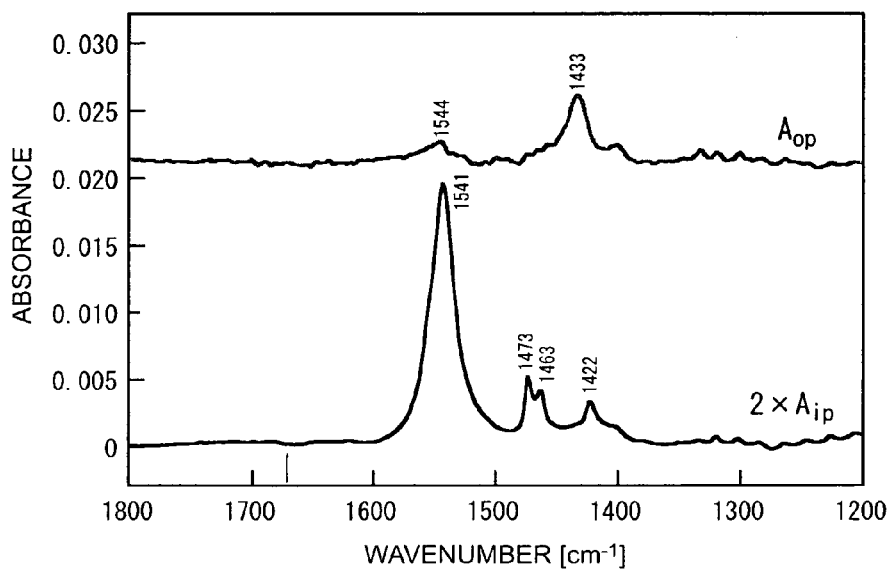
FIG. 6 is a graph showing MAIRS spectra as a result of measuring a predetermined sample with the use of the spectrometric analyzing device according to the invention.
Figure 7:
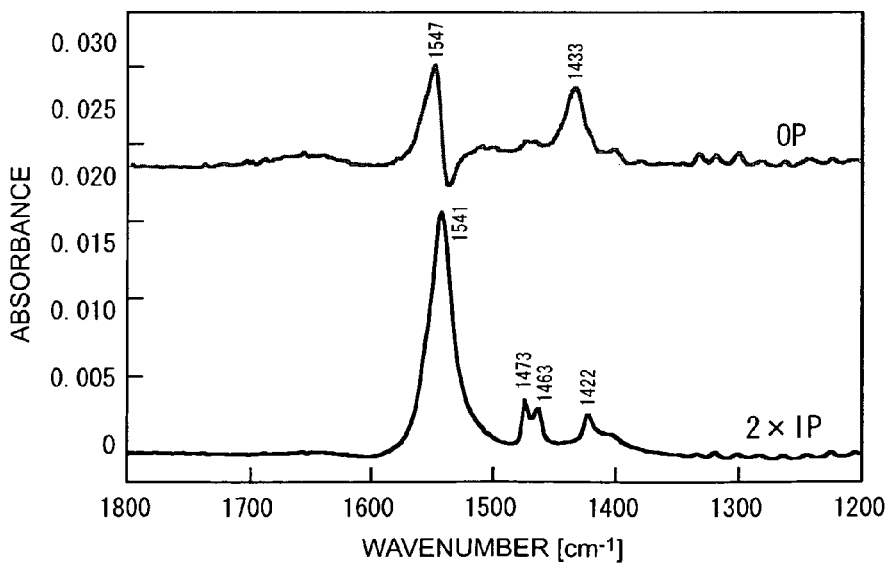
FIG. 7 is a graph showing MAIRS spectra as a result of measuring the same sample as used in the measurement in FIG. 6, according to the conventional multiple-angle incidence resolution spectrometry.

| | |
|---|---|
| 1: | Light source |
| 2: | Polarizing filter |
| 3: | Detection unit |
| 4: | Regression operation unit |
| 5: | Absorbance spectrum calculation unit |
| 6: | Thin film |
| 7: | Supporting member |

What is claimed is:

1. A spectrometric analyzing device for analyzing a thin film on a supporting member that is optically transparent to incident light, the device comprising:

a light source capable of emitting light to a measurement portion to be measured, at n different angles of incidence, $\theta_n$;

a polarizing filter provided between the light source and the measurement portion and shielding an s-polarized component of the light emitted from the light source;

a detection unit receiving transmitted light transmitted through the measurement portion, thereby detecting transmission spectra, S;

a regression operation unit obtaining an in-plane mode spectrum, $S_{ip}$, and an out-of-plane mode spectrum, $S_{op}$, through a regression analysis, by using the transmission spectra, S, detected by the detection unit for the transmitted light at each of the n different angles of incidence from the light source, and by using a mixing ratio, R, of the in-plane mode spectrum, $S_{ip}$, and the out-of-plane mode spectrum, $S_{op}$, for each of the angles of incidence, the regression operation unit using a regression formula below:

$$\begin{pmatrix} S_{ip} \\ S_{op} \end{pmatrix} = (R^T R)^{-1} R^T S$$

where superscript, T, denotes a transposed matrix and superscript, −1, denotes an inverse matrix, the mixing ratio, R, is expressed by a matrix below:

$$R = C \begin{pmatrix} \cos^2\theta_1 + \sin^2\theta_1 \tan^2\theta_1 & \tan^2\theta_1 \\ \cos^2\theta_2 + \sin^2\theta_2 \tan^2\theta_2 & \tan^2\theta_2 \\ \vdots & \vdots \\ \cos^2\theta_j + \sin^2\theta_j \tan^2\theta_j & \tan^2\theta_j \\ \vdots & \vdots \\ \cos^2\theta_n + \sin^2\theta_n \tan^2\theta_n & \tan^2\theta_n \end{pmatrix}$$

where C denotes a constant and $\theta_j$ denotes a j-th angle of incidence among the n different angles of incidence of the light from the light source; and an absorbance spectrum calculation unit calculating an in-plane mode absorbance spectrum, $A_{ip}$, and an out-of-plane mode absorbance spectrum, $A_{op}$, of the thin film, based on the in-plane mode spectrum, $S_{ip}$, and the out-of-plane mode spectrum, $S_{op}$, which are obtained by the regression operation unit in each of a state in which the thin film is on the supporting member and a state in which no thin film is on the supporting member.

2. The spectrometric analyzing device according to claim 1, in which the absorbance spectrum calculation unit calculates the in-plane mode absorbance spectrum, $A_{ip}$, and the out-of-plane mode absorbance spectrum, $A_{op}$, of the thin film, in a manner that the in-plane mode spectrum, $s_{sip}$, and the out-of-plane mode spectrum, $s_{sop}$, which are obtained with the thin film on the supporting member are respectively divided by the in-plane mode spectrum, $s_{bip}$, and the out-of-plane mode spectrum, $S_{bop}$, which are obtained without the thin film on the supporting member, thereby obtaining logarithms.

3. The spectrometric analyzing device according to claim 1, in which the light source is capable of emitting the light at the n different angles of incidence, $\theta_n$, within a range from greater than 0° to smaller than an angle at which a sum of a reflectance of the s-polarized component and a reflectance of a p-polarized component of the supporting member begins to exhibit great variation in relation to the angles of incidence.

4. The spectrometric analyzing device according to claim 1, in which the light source is capable of emitting light having an arbitrary wavelength which is optically transparent to the supporting member.

5. A spectrometric analyzing method for analyzing a thin film on a supporting member that is optically transparent to incident light, the method comprising:
- a step of emitting light from a light source to a measurement portion to be measured, at n different angles of incidence, $\theta_n$;
- a step of shielding an s-polarized component of the light emitted from the light source, by using a polarizing filter provided between the light source and the measurement portion;
- a detection step of receiving transmitted light transmitted through the measurement portion, thereby detecting transmission spectra, S;
- a regression operation step of performing a regression analysis, to obtain an in-plane mode spectrum, $S_{ip}$, and an out-of-plane mode spectrum, $S_{op}$, by using the transmission spectra, S, detected by the detection step for the transmitted light at each of the n different angles of incidence from the light source, and by using a mixing ratio, R, of the in-plane mode spectrum, $S_{ip}$, and the out-of-plane mode spectrum, $S_{op}$, for each of the angles of incidence, the regression operation step using a regression formula below:

$$\begin{pmatrix} S_{ip} \\ S_{op} \end{pmatrix} = (R^T R)^{-1} R^T S$$

where superscript, T, denotes a transposed matrix and superscript, −1, denotes an inverse matrix, the mixing ratio, R, is expressed by a matrix below:

$$R = C \begin{pmatrix} \cos^2\theta_1 + \sin^2\theta_1 \tan^2\theta_1 & \tan^2\theta_1 \\ \cos^2\theta_2 + \sin^2\theta_2 \tan^2\theta_2 & \tan^2\theta_2 \\ \vdots & \vdots \\ \cos^2\theta_j + \sin^2\theta_j \tan^2\theta_j & \tan^2\theta_j \\ \vdots & \vdots \\ \cos^2\theta_n + \sin^2\theta_n \tan^2\theta_n & \tan^2\theta_n \end{pmatrix}$$

where C denotes a constant and $\theta_j$ denotes a j-th angle of incidence among the n different angles of incidence of the light from the light source; and an absorbance spectrum calculation step of calculating an in-plane mode absorbance spectrum, $A_{ip}$, and an out-of-plane mode absorbance spectrum, $A_{op}$, of the thin film, based on the in-plane mode spectrum, $S_{ip}$, and the out-of-plane mode spectrum, $S_{op}$, which are obtained in each of a state in which the thin film is on the supporting member and a state in which no thin film is on the supporting member through the regression operation step.

6. The spectrometric analyzing method according to claim 5, in which the absorbance spectrum calculation step calculating the in-plane mode absorbance spectrum, $A_{ip}$, and the out-of-plane mode absorbance spectrum, $A_{op}$, of the thin film, in a manner that the in-plane mode spectrum, $s_{sip}$, and the out-of-plane mode spectrum, $s_{sop}$, which are obtained with the thin film on the supporting member are respectively divided by the in-plane mode spectrum, $s_{bip}$, and the out-of-plane mode spectrum, $S_{bop}$, which are obtained without the thin film on the supporting member, thereby obtaining logarithms.

7. The spectrometric analyzing method according to claim 5, in which the light source is capable of emitting the light at the n different angles of incidence, $\theta_n$, within a range from 0° to smaller than an angle at which a sum of a reflectance of the s-polarized component and a reflectance of a p-polarized component of the supporting member begins to exhibit great variation with an increase of the angles of incidence.

8. The spectrometric analyzing method according to claim 5, in which the light source is capable of emitting light having an arbitrary wavelength which is optically transparent to the supporting member.

\* \* \* \* \*

UNITED STATES PATENT AND TRADEMARK OFFICE
CERTIFICATE OF CORRECTION

| | |
|---|---|
| PATENT NO. | : 8,094,308 B2 |
| APPLICATION NO. | : 12/310865 |
| DATED | : January 10, 2012 |
| INVENTOR(S) | : Takeshi Hasegawa |

It is certified that error appears in the above-identified patent and that said Letters Patent is hereby corrected as shown below:

Column 3, line 62 – Replace "step 6*f* emitting" with --step of emitting--

Signed and Sealed this
Twenty-ninth Day of January, 2013

David J. Kappos
*Director of the United States Patent and Trademark Office*